United States Patent [19]

Reinartz et al.

[11] Patent Number: 5,739,403
[45] Date of Patent: Apr. 14, 1998

[54] PROCESS FOR THE PRODUCTION OF OPTIONALLY SUBSTITUTED 4-AMINODIPHENYLAMINES

[75] Inventors: Klaus Reinartz, Köln; Adolf Brill, Kellinghusen; Fred Schuhmacher, Schenefeld, all of Germany

[73] Assignee: Bayer AG, Leverkusen, Germany

[21] Appl. No.: 778,838

[22] Filed: Jan. 6, 1997

[30] Foreign Application Priority Data

Jan. 11, 1996 [DE] Germany .................. 19 600 722.4

[51] Int. Cl.$^6$ .................................................. C07C 209/36
[52] U.S. Cl. .................. 564/423; 564/408; 564/470; 564/471; 564/472; 564/433; 564/434
[58] Field of Search ......................... 564/408, 420, 564/421, 422, 423, 433, 434

[56] References Cited

U.S. PATENT DOCUMENTS

| | | | |
|---|---|---|---|
| 5,117,063 | 5/1992 | Stern | 564/395 |
| 5,453,541 | 9/1995 | Stern et al. | 564/398 |
| 5,608,111 | 3/1997 | Stern et al. | 564/398 |

FOREIGN PATENT DOCUMENTS

| | | |
|---|---|---|
| 184914 | 11/1985 | European Pat. Off. . |
| 974082 | 1/1964 | United Kingdom . |

*Primary Examiner*—Richard L. Raymond
*Attorney, Agent, or Firm*—Connolly and Hutz

[57] ABSTRACT

4-Aminodiphenylamines are produced by reacting optionally substituted aniline with optionally substituted nitrobenzene in the presence of water and/or alcohols and organic and/or inorganic bases and then catalytically hydrogenating the resultant nitro- and/or nitrosodiphenylamine in the presence of water, wherein the catalytic hydrogenation of the reaction mixture is performed in the presence of 25 to 80 wt. % of water, relative to the weight of the reaction mixture from the condensation reaction, the hydrogenation catalyst is removed from the hydrogenation mixture once absorption of hydrogen has ceased, 10 to 100 vol. % of aromatic solvent, relative to the total volume of the hydrogenation mixture, are optionally added to the hydrogenation mixture, the resultant organic phase is separated in order to isolate the 4-aminodiphenylamine and the aqueous phase is returned to the initial reaction mixture.

6 Claims, No Drawings

PROCESS FOR THE PRODUCTION OF OPTIONALLY SUBSTITUTED 4-AMINODIPHENYLAMINES

This invention relates to a process for the production of optionally substituted 4-aminodiphenylamines (4-ADPA) by the reaction of optionally substituted anilines with optionally substituted nitrobenzenes and subsequent catalytic hydrogenation of the resultant nitro- and/or nitrosodiphenylamines.

U.S. Pat. No. 5,117,063 describes a process for the production of 4-aminodiphenyl-amines by reacting optionally substituted anilines with optionally substituted nitrobenzene in the presence of protic solvent and inorganic and/or organic bases and hydrogenating the resultant nitro- and/or nitrosodiphenylamines optionally in the presence of water. According to example 1 of the cited U.S. patent, the catalytic hydrogenation is performed in the presence of 16 ml of water (approx. 10 vol. %). In this reaction, the yield of 4-aminodiphenylamine, relative to the introduced nitrobenzene, is reported to be 85% of theoretical.

Apart from the only unsatisfactory yield of 4-aminodiphenylamine, the process described in the stated U.S. patent has the further disadvantage that, due to the small proportion of water, the introduced inorganic or organic base may be recovered only incompletely. This reduces the economic viability of the process described therein. Since, according to the process of U.S. Pat. No. 5,117,063, the introduced base may be recovered only incompletely, the remaining base remains in the crude mixture, which may result in the formation of unwanted secondary or decomposition products during working up of the crude mixture.

The object of the present invention was accordingly to avoid the above-stated disadvantages of the process described in U.S Pat. No. 5,117,063 and to provide a process in which the introduced basic catalyst may virtually completely be returned into the reaction mixture used. The process according to the invention should moreover result in elevated yields of 4-aminodiphenylamines and virtually no secondary or decomposition products should be formed during working up.

The present invention accordingly provides a process for the production of optionally substituted 4-aminodiphenylamine by the reaction of optionally substituted aniline with optionally substituted nitrobenzene in the presence of water and/or alcohols and inorganic and/or organic bases and subsequent catalytic hydrogenation of the resultant nitro- and/or nitrosodiphenylamine in the presence of water, which process is characterised in that the catalytic hydrogenation is performed in the presence of 25 to 80 wt. % of water, relative to the weight of the reaction mixture from the condensation reaction, the hydrogenation catalyst is removed from the hydrogenation mixture once absorption of hydrogen has ceased, the resultant organic phase is separated in order to isolate the 4-amino-diphenylamine and the aqueous phase is returned to the initial reaction mixture.

In the process according to the invention, hydrogenation is preferably performed in the presence of 30 to 50 wt. % of water, relative to the total weight of the reaction mixture.

Once the hydrogenation catalyst has been removed from the hydrogenation mixture, 10 to 100 vol. %, in particular 10 to 80 vol. %, relative to the total volume of the hydrogenation mixture, of an aromatic solvent are preferably apportioned to the hydrogenation mixture. Aromatic solvents which may be mentioned are benzene, toluene and/or xylene, preferably toluene.

Optionally substituted anilines which may be used in the process according to the invention are: aniline, o-, m- or p-methylaniline; o-, m- or p-ethylaniline; o-, m- or p-methoxyaniline, preferably aniline.

Optionally substituted nitrobenzenes which may be used in the process according to the invention are: nitrobenzene; o- or m-methylnitrobenzene; o- or m-ethylnitro-benzene; o- or m-methoxynitrobenzene, in particular nitrobenzene.

In the process according to the invention, 1 to 10, in particular 3 to 6 mol of aniline are conventionally used per mol of nitrobenzene.

It is important for the process according to the invention that the reaction is performed in the presence of protic solvents such as water and/or alcohols, such as methanol or ethanol. The quantity of protic solvent should here not exceed 8 vol. %, relative to the total volume of the reaction mixture. The quantity of protic solvent used should advantageously amount to no more than 4 vol. %. The quantity of protic solvent introduced is dependent upon any additionally introduced solvents such as dimethyl sulphoxide, dimethylformamide, pyridine, toluene and/or hexane and is readily determined by preliminary testing.

The process according to the invention is preferably performed in the presence of water and/or methanol, in particular in the presence of water. The optimum mixing ratio may be determined by appropriate preliminary testing.

Inorganic and/or organic bases which are suitable for the process according to the invention are in particular: alkali metals, alkali metal hydroxides, tetra-substituted ammonium hydroxides, optionally also in the presence of phase transfer catalysts. Tetraalkylammonium hydroxides are very particularly preferred, in particular tetramethylammonium hydroxide.

The bases are conventionally used in quantifies of 1 to 4 mol, preferably of 1 to 1.5 mol, relative to 1 mol of nitrobenzene, wherein the molar ratio of protic solvent to base is conventionally 1:1 to 4:1.

The reaction of the optionally substituted aniline with the optionally substituted nitrobenzene is generally performed at temperatures of 50° C. to 100° C., preferably of 60° C. to 80° C. The reaction is performed under reduced pressure, i.e. at pressures of 20 to 150 mbar, preferably of 70 to 80 mbar.

It is possible using the process according to the invention to subject the reaction mixture obtained from the reaction of the stated anilines with the stated nitrobenzenes directly to catalytic hydrogenation. It is, of course, also possible to isolate the resultant intermediate products, i.e. nitro- and/or nitrosodiphenylamines, in a suitable manner and then to subject them to catalytic hydrogenation. When isolating the nitro- and/or nitrosodiphenylamines, which are initially obtained in salt form, it is possible to convert the salts into free compounds by hydrolysis and then to subject the free compounds to catalytic hydrogenation.

Preferably, however, the process according to the invention is performed by directly subjecting the resultant nitro- and/or nitrosodiphenylamines to catalytic hydrogenation in the presence of water and/or alcohols.

The hydrogenation according to the invention may be performed with conventional hydrogenation catalysts, such as noble metals on activated carbon, Raney nickel, Raney copper, preferably noble metals on activated carbon, in particular platinum on activated carbon. Such hydrogenation catalysts are described, for example, in *Ullmanns Encyklopä, die der technischen Chemie*, 4th edition, volume 13, p. 141.

The introduced quantity of hydrogenation catalyst is conventionally 0.1 to 1 wt. %, relative to the substance to be hydrogenated.

Catalytic hydrogenation is performed at temperatures of 50° C. to 150° C., preferably of 60° C. to 80° C. Hydrogen pressure is approximately 1 to 25, in particular 10 to 15 bar.

Once hydrogen absorption has ceased, the hydrogenation catalyst is removed from the hydrogenation mixture, for example by filtration. The above-stated quantity of aromatic solvent is then optionally added to the hydrogenation mixture, the resultant organic phase is separated in the conventional manner in order to isolate the 4-aminodiphenylamine and the aqueous phase, which contains the organic and/or inorganic bases, is returned to the initial reaction mixture.

By using the process according to the invention, 4-aminodiphenylamine is obtained in a yield of at least 86% of theoretical, in particular of at least 90% of theoretical. At least 99% of the introduced organic and/or inorganic base is recovered. It is particularly significant that the hydrogenation according to the invention, in which a higher content of water is used than in the prior art, provides a considerably shorter reaction time and a substantial increase in the field of hydrogenation product.

EXAMPLES

Example 1

18.7 kg of a 25% aqueous tetramethylammonium hydroxide solution (TMAOH) are concentrated by distillation at a temperature of 55° C. and a pressure of 75 mbar to yield a 35% solution.

After adding 26.9 L of aniline, an aniline/water azeotrope is distilled off at a temperature of 75° C. and a pressure of 75 mbar until the molar ratio of water:base is approximately 4:1. 6.0 kg of nitrobenzene are then pumped in under the same conditions within 3 hours and the mixture stirred for a further 4 hours. Distillation of a water/aniline azeotrope continues during this period.

220 g of Pt/C catalyst (5% Pt) and 12 L of water are added to this crude mixture. At a temperature of 80° C., the pressure is then raised to at most 15 bar with hydrogen and the reaction mixture stirred until no further absorption of hydrogen is observed. According to HPLC the yield of hydrogenation products was quantitative. In this test procedure the reaction time is 4 hours. 10 L of toluene are added, the catalyst filtered out and the organic and aqueous phase separated in a separating vessel.

The organic phase is then worked up by fractional distillation. The pure yield of 4-ADPA is 91%, relative to the introduced nitrobenzene.

Analysis of the aqueous phase shows that 99.7% of the introduced tetramethyl-ammonium hydroxide may be isolated. The resultant aqueous phase may be returned to the reaction without loss of reactivity.

Example 2

Aniline and nitrobenzene are reacted in the presence of tetramethylammonium hydroxide in a similar manner as in Example 1.

A quantity of water (see Table) is added to this crude mixture and the Pt/C catalyst added. The batch is hydrogenated at a temperature of 80° C. at a hydrogen pressure of at most 15 bar until no further absorption of hydrogen can be observed.

Toluene is then added and the catalyst removed. The aqueous and the organic phase are separated. The organic phase is optionally washed with fresh water until the tetramethylammonium hydroxide has been extracted in its entirety.

The organic phase is then fractionally distilled. The pure yields of 4-ADPA, relative to introduced nitrobenzene, are shown in the following table.

TABLE

| Quantity of water relative to introduced crude mixture wt. % | Pure yield of 4-ADPA, relative to introduced nitrobenzene % |
|---|---|
| 10* | 83 |
| 20* | 84 |
| 30 | 92 |
| 33 | 91 |
| 50 | 88 |
| 70 | 86 |
| 80 | 86 |
| 100* | 82 |

*not according to the invention

We claim:

1. Process for the production of optionally substituted 4-aminodiphenylamine by the reaction of optionally substituted aniline with optionally substituted nitrobenzene in the presence of water and/or alcohols and organic and/or inorganic bases and subsequent catalytic hydrogenation of the resultant nitro- and/or nitrosodiphenylamine in the presence of water, characterised in that catalytic hydrogenation of the reaction mixture is performed in the presence of 25 to 80 wt. % of water, relative to the weight of the reaction mixture from the condensation reaction, the hydrogenation catalyst is removed from the hydrogenation mixture once absorption of hydrogen has ceased, the resultant organic phase is separated in order to isolate the 4-aminodiphenylamine and the aqueous phase is returned to the initial reaction mixture.

2. Process according to claim 1, characterised in that the catalytic hydrogenation is performed in the presence of 30 to 50 wt. % of water.

3. Process according to claim 1, characterised in that 10 to 100 vol. % of aromatic solvent are added to the hydrogenation mixture.

4. Process according to claim 1, characterised in that the reaction of the aniline with nitrobenzene is performed at temperatures of 50 ° C. to 100° C.

5. Process according to claim 1 characterised in that 1 to 10 tool of aniline are used per tool of nitrobenzene.

6. Process according to claim 1, characterized in that the catalytic hydrogenation is performed in the presence of 30 to 80 L wt. % of water.

* * * * *